United States Patent [19]

Zupancic et al.

[11] 4,230,884

[45] Oct. 28, 1980

[54] PROCESS FOR PREPARING 2-(3-BENZOYLPHENYL)-PROPIONIC ACID

[75] Inventors: Boris Zupančič; Mirko Sopčič, both of Ljubljana, Yugoslavia

[73] Assignee: LEK, tovarna farmacevtskih in kemicnih izdelkov, n.sol.o., Ljubljana, Yugoslavia

[21] Appl. No.: 28,779

[22] Filed: Apr. 10, 1979

[30] Foreign Application Priority Data

Apr. 10, 1978 [YU] Yugoslavia .............................. 853/78

[51] Int. Cl.$^3$ ............................................. C07C 59/84
[52] U.S. Cl. ..................................................... 562/460
[58] Field of Search ......................................... 562/460

[56] References Cited

FOREIGN PATENT DOCUMENTS 1164585  9/1969  United Kingdom ...................... 562/460

*Primary Examiner*—Paul J. Killos
*Attorney, Agent, or Firm*—Pollock, Vande Sande and Priddy

[57] ABSTRACT

Process for preparing 2-(3-benzoylphenyl)-propionic acid or salt thereof which includes methylating 3-benzoyl-phenyl acetonitrile or an alkoxide thereof in the presence of neutral non-cyclic ligands with an open polyether chain.

5 Claims, No Drawings

PROCESS FOR PREPARING 2-(3-BENZOYLPHENYL)-PROPIONIC ACID

In our basic patent application Ser. No. 842,824, filed on Oct. 17, 1977, there was described a new process for preparing 2-(3-benzoylphenyl)-propionic acid, which is performed in accordance with the following reaction scheme:

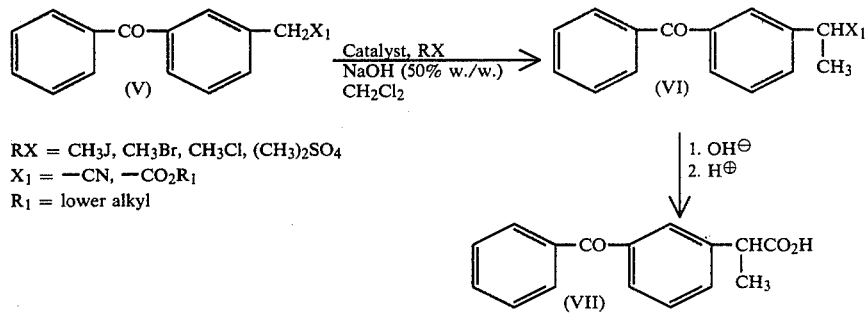

RX = $CH_3J$, $CH_3Br$, $CH_3Cl$, $(CH_3)_2SO_4$
$X_1 = -CN, -CO_2R_1$
$R_1$ = lower alkyl The methylation is performed in the presence of a catalyst, under conditions corresponding to the so-called Phase Transfer Catalysis [Norio Sugimoto et al, Chem. Pharm. Bull. 10, 427 (1962); M. Makosza, B. Serafimova, Roczniki chemii ann. soc. chim. Polonorum, 39, 1401 (1965); A. Brändström, U. Junggren, Tetrahedron Letters, 473 (1972); Charles M. Starks, Donald R. Napier, British patent 1,227,144 (7th Apr. 1971); Eckehard V. Demlow, Angew. Chem. 86, 187 (1974); Jozef Dockx, Synthesis, 8, 441 (1973)].

In the process of the basic application, as catalysts were used ammonia quaternary compounds, e.g. benzyltriethyl ammonium chloride, tetrabutyl ammonium hydrogensulfate and tricaprilylmethyl ammonium chloride.

It has now been found that the above-described process may be even more successfully and economically performed, if as catalysts there are chosen neutral non-cyclic ligands with an open polyether chain, the so-called podands. The structure of podands is close to that of crown-ethers, which are well-known complex-forming substances.

Hitherto there has also been known the use of podands in the substitution of halogens with cyanide, acetate, sulfhydryl or azide ions (L. Lehmkuhl et al, Synthesis, 1977, p. 184).

In accordance with the present invention, they are used for the first time in C-alkylation.

From the neutral non-cyclic ligands with an open chain, for the aim of the present invention there are especially suitable the easily available oligoethylene glycols (e.g. Polydiol-400, Teol, Ljubljana, Yugoslavia), their monoethers of the general formula

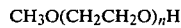

wherein $2 \leq n$ (available on the market as e.g. Polyglykol M 500, Hoechst, Germany), or their diethers of the general formula

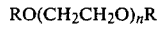

wherein $2 \leq n$ and R stands for a $C_{1-4}$-alkyl, preferably methyl (generic name "Glyme"), optionally in a mixture thereof.

The average molecular weight of oligoethylene glycols and their mono- or diethers, which can be used in accordance with the present invention, should be preferably within the range of 200 to 4000.

The reaction is performed in a somewhat wider temperature range than in the process of the basic application, namely at $-10°$ to $+50°$ C. in a system solid/liquid or liquid/liquid. Like in the basic process, also in the present case the choice of the reaction medium is not critical, yet there may be suitable the presence of solvents, chosen from the group of chlorinated aliphatic hydrocarbons, chlorinated aromatic hydrocarbons, aromatic hydrocarbons, e.g. toluene, or aliphatic hydrocarbons or esters, e.g. ethylacetate.

The obtained mono- or dimethylated product is subsequently subjected to acidic or alkaline hydrolysis and the resulting 2-(3-benzoylphenyl)-propionic acid is optionally converted into a metal salt or an addition salt of a nitrogen-containing base.

The purification is performed in a conventional manner, e.g. by means of chromatography, fractional precipitation, fractional distillation of the intermediates, and in the final step by means of crystallization from acetonitrile or a petrolether/benzene or acetone/water mixture.

The inventive process is illustrated by the following examples.

EXAMPLE 1

Methylation of 3-cyanomethylbenzophenone in a system solid/liquid

In a four-necked flask of 250 ml, equipped with a stirrer, thermometer, reflux cooler and cooling bath, there are charged under stirring 70.56 g of 3-cyanomethylbenzophenone (m.p. $>50°$ C., GC approx. 91%) and 70 ml of toluene at $30°$ to $40°$ C. to dissolve the reactants, subsequently it is cooled down to $20°$ C., 61.56 g of powdered NaOH (97%) are added and it is stirred for 30 minutes. Thereupon there are added 15.31 g of the catalyst (oligoethylene glycoldimethylether with a rel. molecular mass of 400) and the reaction mixture is cooled down to $0°$ C. Subsequently there are added 30.3 ml of dimethylsulfate, diluted with an equal volume of toluene at $0°$ C. during 90 minutes, whereupon it is stirred for further 40 minutes. The reaction is controlled by means of thin-layer chromatography. Subsequently, to the reaction mixture warmed up to $20°$ C., there are added 12.28 g of benzaldehyde in 25 ml of toluene within 15 minutes, it is stirred on for 1 hour and finally diluted with 450 ml of water.

The aqueous layer is separated and shaken with 50 ml of toluene, the toluene layer is transferred into a flask of 1 l, equipped with a stirrer, and there are added 200 ml of HCl (1:5) under stirring. After 15 minutes of stirring, the toluene layer is separated, washed with 200 ml of water and dried (Na$_2$SO$_4$) overnight. Subsequently Na$_2$SO$_4$ is filtered off and the toluene is evaporated in a rotation evaporator within one hour at T$_{max}$. 80° C.

Into a Bredt vacuum apparatus there are charged 74.7 g of the distillation residue and the following fractions are distilled off at said conditions:

| Ist fraction up to 86° C. | (vapour temp.) P: | 0.05 mmHg | 3.48 g |
|---|---|---|---|
| IInd fraction up to 166° C. | | 0.02 | 0.17 g |
| IIIrd fraction up to 238° C. | | 0.1 | 61.1 g (81.53 %) |
| IVth fraction up to 234° C. | | 0.2 | 6.2 g Duration of the distillation approx. 50 min. |
| Resinous residue | | | approx. 1 g |

Hydrolysis of the resulting 3-benzoylphenylpropionitrile 61.1 g of 3-benzoylphenylpropionitrile, resulting from the distillation, are transferred into a four-necked reaction flask of 1 l, equipped with a stirrer, thermometer, reflux cooler and heating pad, subsequently there are added 660 ml of a mixture of ethanol/water (1:1) and under stirring 22.45 g of KOH during 10 minutes, following the heating of the reaction mixture up to 65° C. It is heated up to the boiling point (approx. 82° C.), whereupon it is stirred under reflux cooling for 24 hours and finally it is evaporated in a rotation evaporator. There results a smeary residue which is put into a flask of 1 l, equipped with a stirrer, diluted with 450 ml of water and stirred for one hour at ambient temperature untill substantially all residue is dissolved. The orange-brown mixture is separated on a suction filter from the undissolved residue (5.83 g), extracted three times with dichloromethane (with portions of 75, 75 and 50 ml) and decolourized by the addition of 2% of active carbon (with respect to the total weight) at 70° C. and during stirring for 1 hour. There follows a second decolourization with 1.5% of active carbon (with respect to the total weight) and a second filtration. The light-yellow solution is transferred into a beaker of 1 l, there are added 75 ml of dichloromethane, whereupon it is precipitated with conc. HCl (32 ml) under stirring at a temperature of 0° to +5° C. The reaction mixture, acidified to a pH value of 1, is poured into a separatory funnel and the bottom layer is separated. The aqueous layer is shaken with further 30 ml of dichloromethane and combined with the main fraction. Subsequently, the dichloromethane is evaporated on a rotation evaporator at ambient temperature and finally at 70° C. in vacuo (1 hour). The yield is 51.67 g of a yellow-orange oil (78.18%), which is crystallized from acetonitrile.

In a flask of 250 ml, 51.67 g of the crude product are dissolved in 57.17 ml of acetonitrile, 1.56 g of active carbon (1.5% with respect to the total weight) are added, whereas 10 ml of acetonitrile are left for the washing of the filter (total 1.3 ml of acetonitrile/g). The decolourization is performed in 30 minutes, whereupon the carbon is filtered off, the first crystals precipitate at ambient temperature, whereas substantially the whole product crystallizes after 10 minutes in the freezer. The following day it is aspirated and digested in 50 ml of petrolether at ambient temperature, cooled in a freezer and subsequently aspirated. After drying in a vacuum drying oven, there are obtained 40 g (77.6%) of a slightly yellow product, m.p. 88° to 94° C.

The second crystallization requires 52 ml of acetonitrile (1.3 ml/1 g) and 1.2 g of carbon under the same conditions and in the same way (50 ml of petrolether for the digestion) and there result 32.4 g (81.2%) of 2-(3-benzoylphenyl)propionic acid, m.p. 92.5° to 94.5° C. (Kofler).

Contents:
99.8% (titrimetric)
98.4% (GC)

EXAMPLE 2

Methylation of 3-cyanomethylbenzophenone in a system liquid/liquid

Into a four-necked reaction flask of 250 ml, equipped with a stirrer, thermometer, reflux cooler, dropping funnel and cooling bath, there is charged a mixture of 70.56 g of 3-cyanomethylbenzophenone (m.p. 50° C., GC~90%), 15.31 g of oligoethylene glycoldimethylether (rel. mol. mass 400) and 100 ml of toluene and it is stirred at 30° to 40° C. until dissolving (approx. for 20 minutes). It is cooled down to 0° C. and there are added 28.8 ml of dimethylsulfate and during 100 minutes 84 ml of conc. NaOH (approx. 50% w./w. or g/100 g). After the last addition of the hydroxide solution, it is stirred on for half an hour. The performance of the reaction is controlled by thin-layer chromatography (and NMR).

Subsequently, it is heated to 20° C. and there is added during 15 minutes under stirring drop by drop a solution of 12.28 g of benzaldehyde in 25 ml of toluene. Then it is diluted with 450 ml of water in a separating funnel of 1 l. The aqueous phase is separated and shaken with further 50 ml of toluene, the combined toluene layers are transferred into a flask of 1 l and treated with 200 ml of conc. HCl (1:5). After 15 minutes of stirring, the toluene layer is separated, washed with 200 ml of water and dried (Na$_2$SO$_4$) overnight. The drying agent is filtered off, whereupon the filtrate is evaporated for 1 hour in a rotation evaporator at a max. temperature of 80° C. in order to obtain 81.26 g of an orange-brown oily residue. Into a Bredt vacuum distillation apparatus there are transferred the above 81.26 g of the orange brown product and separated into the following fractions:

| Ist fraction up to 79° C. | 0.2 mmHg | 3.61 g |
|---|---|---|
| IInd fraction up to 166° C. | 0.2 | 0.06 g |
| IIIrd fraction up to 238° C. | 0.2 | 64.62 g (86.22 %) |
| IVth fraction up to 237° C. | 0.4 | 7.86 g |
| Residue | | 1.1 g |
| Duration of distillation: 55 minutes | | |

Hydrolysis of the obtained 3-benzoylphenylpropionitrile 64.62 g of the IIIrd fraction are poured into a flask of 1 l with 698 ml of ethanol/water (1:1), heated by means of a heating pad to 65° C. and there are added during 10 minutes 13.7 g of KOH. After 24 hours of refluxing (82° C.) it is transferred into a rotation evaporator and evaporated in vacuo until a smeary product is obtained. It is diluted with 450 ml of water and stirred for 1 hour at ambient temperature. The undissolved residue (5.76 g) is aspirated and extracted three times with dichloromethane (portions of 70, 70 and 50 ml). It is transferred into a flask of 1 l, equipped with a stirrer and reflux cooler, there are added 2% of active carbon (with respect to the total weight) and it is stirred for 1 hour at 70° C. The carbon is aspirated and this reaction step is repeated. The decolourized light-yellow solution is cooled down to +5° C. and there are added 75 ml of dichloromethane and subsequently it is precipitated under stirring with 32 ml of conc. HCl (pH 1). The dichloromethane layer is separated, the aqueous phase is shaken with 25 ml of fresh dichloromethane, combined with the main fraction and the solvent is evaporated on a rotation evaporator, at the beginning at ambient temperature and then at 70° C. in vacuo. There are obtained 52.71 g (75.46%) of a crude product as an orange-yellow oil.

After the first crystallization from acetonitrile (requiring 68.52 ml of acetonitrile and 1.59 g of carbon), there are obtained 42.21 g (80%) of the product with a m.p. of 88° to 94° C., whereas the second crystallization yields under similar conditions 34.87 g (82.6%) of the pure 2-(3-benzoylphenyl)-propionic acid with a m.p. of 92° to 94.5° C. In both cases the crystallization is succeeded by digestion with 50 ml of petrolether and subsequently it is dried (cf. Example 1).

Contents:
99.7% theor. (titrimetric)
98.4% (GC)

What is claimed is:

1. Process for preparing 2-(3-benzoylphenyl)-propionic acid or salt thereof wherein 3-benzoylphenyl acetonitrile or an alkoxide thereof comprising 1 to 4 carbon atoms in the alkoxy moiety are reacted with a methylating agent in a two-phase system under conditions of phase transfer catalysis, whereupon the mixture is hydrolysed and optionally the obtained acid is converted into a metal salt or an addition salt of a nitrogen-containing base, characterized in that the methylation is performed in the presence of neutral non-cyclic ligands with an open polyether chain as a catalyst at a temperature within the range of −10° to +50° C.

2. Process according to claim 1, characterized in that the neutral non-cyclic ligands with an open chain are chosen from the group of oligoethylene glycols, their monoethers of the general formula $$CH_3O(CH_2CH_2O)_nH$$

wherein $2 \leq n$, or their diethers of the general formula $$RO(CH_2CH_2O)_nR$$

wherein $2 \leq n$ and R stands for a $C_{1-4}$-alkyl, like methyl, of an average molecular weight within the range of 200 to 4000, or mixtures thereof.

3. Process according to claim 1 wherein the methylation is carried out in the presence of a solvent selected from the group of chlorinated aliphatic hydrocarbon, or chlorinated aromatic hydrocarbon, or aromatic hydrocarbon, or aliphatic hydrocarbon or ester.

4. Process according to claim 1 wherein the methylation is carried out in the presence of toluene or ethyl acetate.

5. Process according to claim 1 wherein 3-cyanomethylbenzophenone is methylated.

* * * * *